United States Patent [19]

Barud

[11] Patent Number: 4,716,581
[45] Date of Patent: Dec. 29, 1987

[54] X-RAY EXAMINATION APPARATUS

[75] Inventor: Sigvard Barud, Jaerfaella, Sweden

[73] Assignee: Siemens Aktiengesellschaft, Berlin and Munich, Fed. Rep. of Germany

[21] Appl. No.: 721,853

[22] Filed: Apr. 9, 1985

[30] Foreign Application Priority Data

Apr. 9, 1984 [DE] Fed. Rep. of Germany ....... 3413348

[51] Int. Cl.⁴ .............................................. H05G 1/02
[52] U.S. Cl. ...................................... 378/198; 378/197
[58] Field of Search ................. 378/11, 15, 17, 38–40, 378/176–179, 189, 190, 193, 195–198

[56] References Cited

U.S. PATENT DOCUMENTS

| 2,818,510 | 12/1957 | Verse | 378/197 |
| 3,803,417 | 4/1974 | Kok | 378/197 |
| 3,824,397 | 7/1974 | Bauer et al. | 378/195 |
| 4,019,059 | 4/1977 | Brundin et al. | 250/451 |
| 4,150,297 | 4/1979 | Borggren | 250/490 |

FOREIGN PATENT DOCUMENTS 2098440 11/1982 United Kingdom .

*Primary Examiner*—Craig E. Church
*Assistant Examiner*—John C. Freeman
*Attorney, Agent, or Firm*—Hill, Van Santen, Steadman & Simpson

[57] ABSTRACT

The invention relates to an x-ray examination apparatus comprising a stand and a support mounting which are adjustable in space, or relative to one another, such that a curved support, mounted on the support mounting is three dimensionally adjustable. At one end of the curved support a radiation source is mounted and at its other end an image layer carrier is mounted so that these units are aligned relative to one another. The support is rotatable about a first shaft. For each of the translational and rotational movements, a drive is provided. In order to obtain an x-ray examination apparatus which is simple in construction and therefore inexpensive, the support is nondisplaceably mounted on the support mounting and is pivotally mounted about an additional shaft disposed horizontally and vertically to the first shaft on the front end of the support mounting.

11 Claims, 5 Drawing Figures

X-RAY EXAMINATION APPARATUS

BACKGROUND OF THE INVENTION

The invention relates to an x-ray examination apparatus comprising a column and a support-mounting which is adjustable in a vertical direction in relation to the column, and which holds a curved support at the one end of which a radiation source and at the other end of which an image layer carrier are mounted in alignment with one another. The support is rotatably mounted about a shaft, and a drive is provided for each of the translational and rotational movements.

U.S. Pat. No. 4,150,297 and British Pat. No. 2,098,440A, both incorporated herein by reference, disclose x-ray examination apparatus of this type wherein an x-ray tube and an x-ray image intensifier are mounted on oppositely disposed ends of a semicircularly curved support. The semicircularly curved support is displaceable on a support-mounting along a track at its circumference. In order that the semicircular support can be satisfactorily displaced in the support mounting, both must be manufactured with high precision. This is costly and makes the x-ray examination apparatus much more expensive.

SUMMARY OF THE INVENTION

An object of the invention is to produce an x-ray examination apparatus of the type initially cited which is simpler in construction and therefore cheaper than the conventional x-ray examination apparatus.

In accordance with the invention, this object is achieved in that the length of the support mounting, i.e. the distance of the front end of the support-mounting from the stand, is adjustable, and that the curved or bent support is pivotally mounted to an additional shaft, disposed horizontally or vertically depending upon orientation relative to the first shaft on the front end of the support mounting. Through these various parts of the x-ray examination apparatus it is no longer necessary to employ an expensive, semicircularly curved support. The support can now be designed in a bent shape in a U- or V-formation, which is far simpler in terms of manufacture and therefore makes the apparatus cheaper. In addition, no curved rail matched to the support is required.

In the case of an x-ray examination apparatus designed in accordance with the invention, it is proposed that the length of the support mounting be adjustable. It is therefore achieved that the stand need be mobile only in one plane. If the support mounting, in addition, is displaceable or pivotal relative to the stand, the necessary movement of the stand is reduced to one direction.

In view of a structurally simple adjustment of the length of the support-mounting it is advisable to design the latter in the form of a telescope. Alternatively, the support mounting can be designed in the form of a two-part articulated arm.

In an expedient embodiment of the invention, it is proposed that the support mounting be pivotally mounted on the stand in a vertical direction about a shaft. This makes it possible for the stand to be kept low.

In order that the support is pivotal in obstructed fashion over a large angular range, in a structurally advantageous embodiment of the invention, the support is laterally secured to the front end of the support mounting.

In an advantageous further development of the invention, it is provided that, for each adjustment movement, rotational movement, or pivot movement, a drive and a position sensor are provided. The signals of the position sensors are transmitted to a control device which, given a specified isocenter, in the case of a position change in one direction determines controlled variables for the other drives in such a fashion that, through their actuation, the isocenter is again adjusted. Through this technique, it is made possible that the support can be controlled in such a fashion that, independently of the course of movement of the x-ray tube, or of the image intensifier respectively, the isocenter can always be maintained.

DESCRIPTION OF THE PREFERRED EMBODIMENTS

Figure 1:
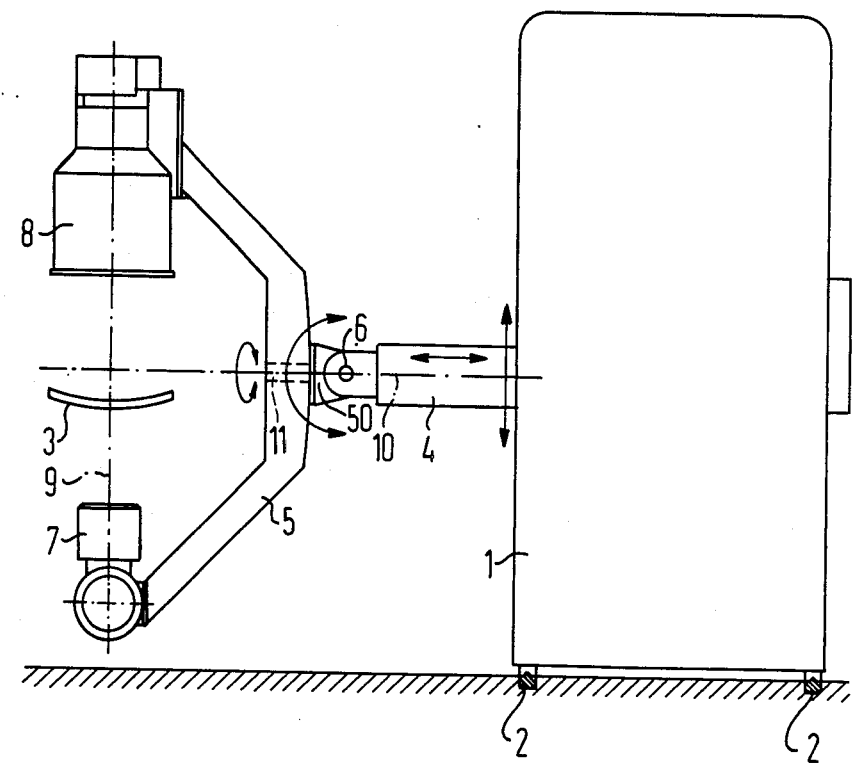
FIG. 1 shows a lateral view of an x-ray examination apparatus in accordance with the invention.

FIG. 1 shows an x-ray examination apparatus comprising a stand 1 which can be guided on floor rails 2 in a longitudinally displaceable fashion and parallel to a patient support table 3.

Vertically adjustably mounted on the stand 1 is a telescopic support mounting 4 for a U- or V-shaped curved or bent support 5. The support is pivotally mounted about a shaft or axle 6, and is secured perpendicularly to the longitudinal direction of the support mounting 4 at its front end via end part 50. The curved support 5 can also be directly secured to the shaft 6. The support 5 is preferably laterally secured on the front end of the support mounting 4. On the one terminating end of the support 5 an x-ray tube 7 is mounted, and on the other terminating end, an image layer carrier 8 is mounted. The x-ray tube 7 is centered with its central ray 9 aimed at the image layer carrier 8. The support is, in addition, rotatably mounted about a shaft or axle 11 which is attached to the end part 50 which is in turn connected by the shaft 6 to an extension of the supporting shaft 10 of the support mounting 4. The support mounting 4 is also designed in the form of a telescope, so that its length in a horizontal direction is adjustable.

Figure 2:
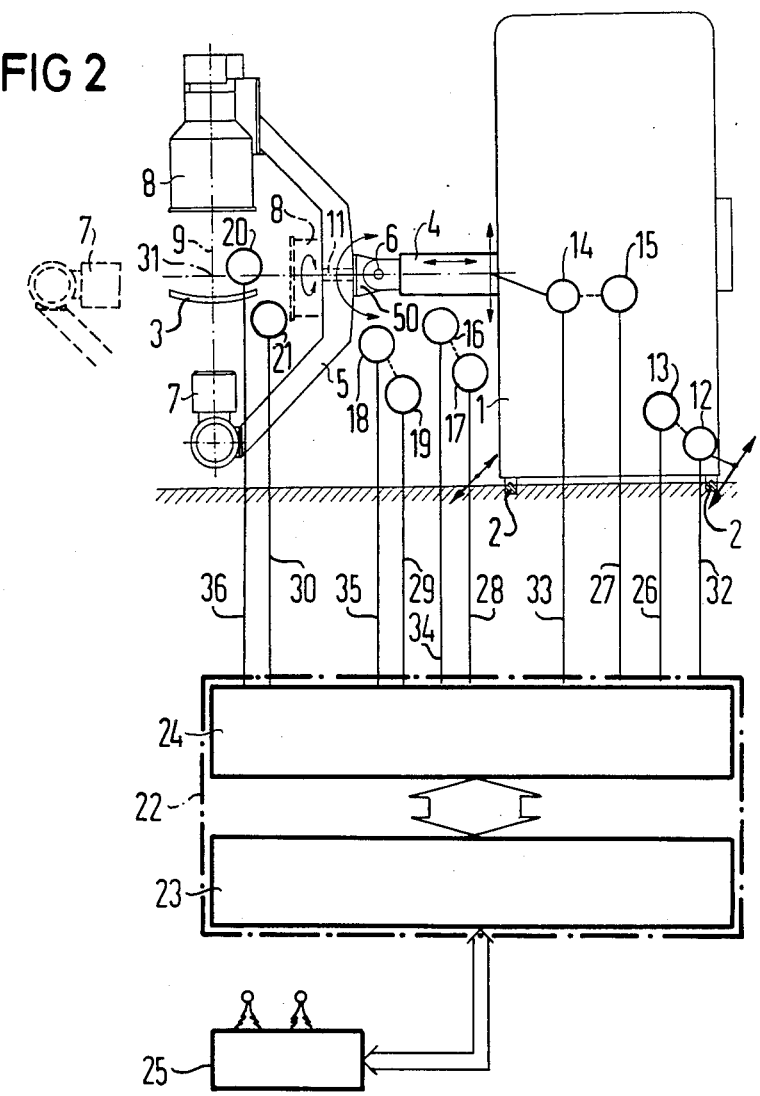
FIG. 2 shows a schematic illustration of a control device for an x-ray examination apparatus in accordance with FIG. 1.

In FIG. 2, it is illustrated that, for each adjustment movement, rotational movement, or pivot movement of the apparatus parts, a drive and a position sensor are provided. Thus, the stand 1 is controlled by a motor 12 and a position sensor 13. The height adjustment of the telescopic support mounting 4 proceeds by use of a motor 14 and a position sensor 15, and the length of the telescopic support mounting 4 is adjusted by a motor 16 and a position sensor 17. An additional motor 18 and the position sensor 19 control the pivot movement of the support 5 about the shaft 6. Finally, a motor 20 and a position sensor 21 for the rotation of the support 4 about the shaft 11 is provided.

Serving as control device 22 for the motors 12, 14, 16, 18, 20, and the position sensors 13, 15, 17, 19, 21, is a computer 23 and a control device 24. Connected to the control device 22 is a control console 25 whereby the position of the x-ray tube 7, or of the image layer carrier 8, are respectively controlled. Such a control device with control console is disclosed in U.S. Pat. No. 4,019,059, incorporated herein by reference, and will therefore not be described in greater detail.

If a position change of the x-ray tube 7, or of the image layer carrier 8 is to be conducted, selective motors 12, 14, 16, 18, and 20 are activated by the control console 25. The signals of the position sensors 13, 15, 17, 19, and 21 are supplied via connections 26-30 to the control installation 22. The control installation 22, then, given a specified isocenter 31, supplies via the connection lines 32-36, control variables to the remaining motors 12, 14, 16, 18, and 20 in such a fashion that, through their activation, the isocenter 31 is maintained. If the support 5 is now to be rotated through 90° so that the x-ray tube 7 and the image layer carrier 8 assume the position illustrated in broken lines, the motor 18 is activated via the control console 25 in order that the support 5 is pivoted about the shaft 6. The control installation 22 then, in the described manner, controls the additional motors 14 and 16 such that the preadjusted isocenter 31 is maintained in the case of the position change of the x-ray tube or of the image layer carrier, respectively. The motors 14 and 16 cause the support-mounting 4 to be lowered and the telescopic arm to be moved outwardly. In a corresponding fashion, in the case of other desired movement paths, also the displacement of the stand 1 is controlled and the support 5 is rotated about the shaft 11. The isocenter 31 need not here be the geometric center between x-ray tube 7 and image intensifier or carrier 8, but can lie in varying positions, depending upon the adjusted enlargement. It is likewise possible, with the aid of the control, to shift the isocenter 31 in a randomly disposed object plane while the enlargement remains the same. With the aid of a memory not illustrated, it is further possible to retain the necessary data for a specific position of the apparatus and, after a random displacement, to automatically again adjust the initial position.

Figure 3:
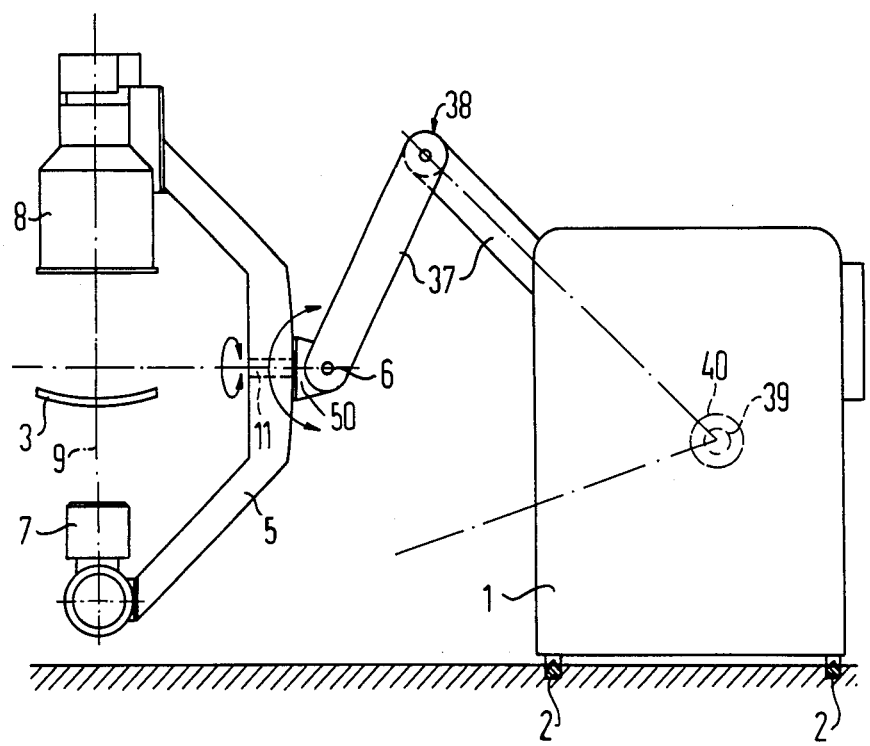
FIGS. 3 through 5 show additional embodiments of an x-ray examination apparatus in accordance with the invention.

In FIG. 3, an additional embodiment of the x-ray examination apparatus of the invention is illustrated. In this sample embodiment, the support 5 is held by means of a two-part articulated arm 37. For the adjustment of the two parts relative to one another, a motor 38 is provided. The further end of the arm 37 is pivotal in the stand 1 about a shaft 39 by means of a motor 40. Associated with the motors 38, 40 are non-illustrated position sensors which are connected to the control installation (FIG. 2). Through the mounting and movement of the arm 37, the stand 1 can be kept low in this embodiment.

Figure 4:
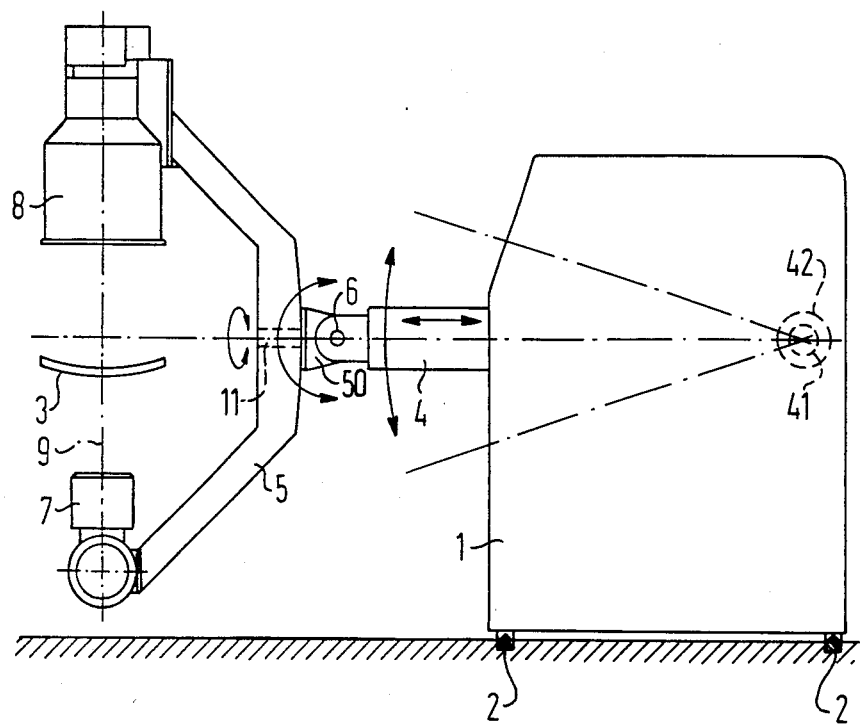

In FIG. 4, the telescopic support mounting 4 is pivotally mounted about a shaft 41 in the stand 1. As a drive and control, a motor 42 and a non-illustrated position sensor are employed, which are connected to the control installation shown in FIG. 2. The stand 1 can also be kept low in this embodiment through the support mounting 4.

Figure 5:
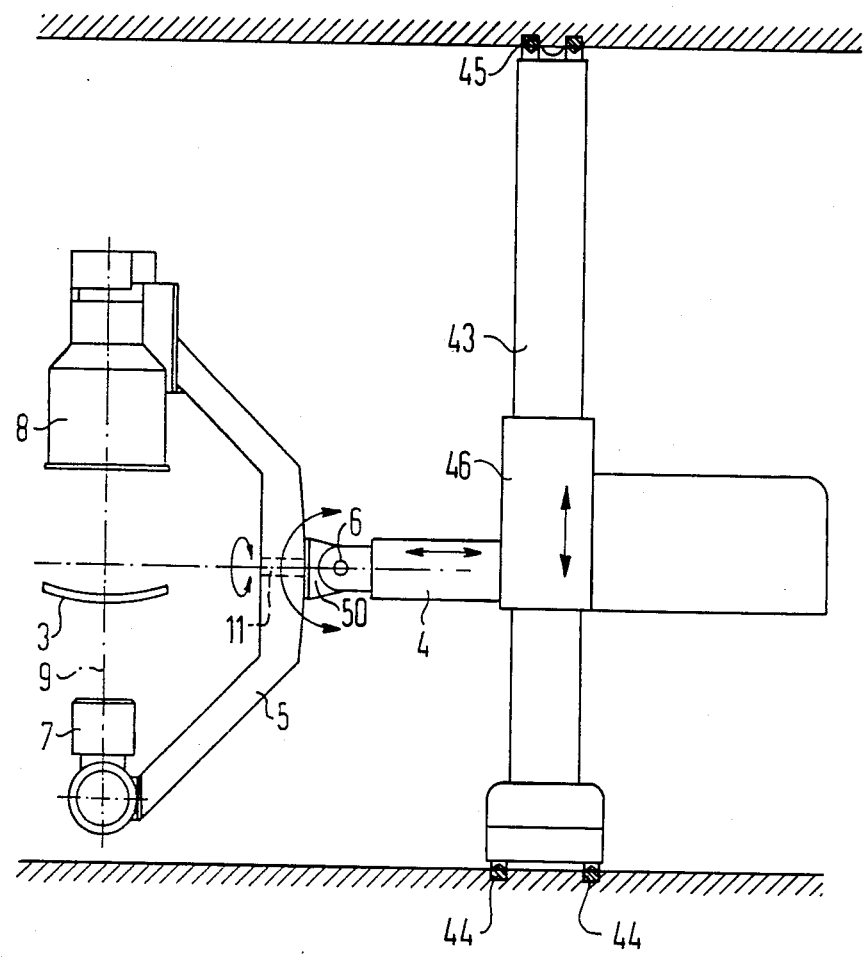

FIG. 5 finally shows an x-ray examination apparatus comprising a stand 43 which runs both on floor rails as well as on ceiling rails 44, 45, and on which a stand carriage 46 is guided in a longitudinally displaceable fashion. The telescopic support mounting 4 is arranged in fixed fashion on the stand carriage 46.

The movement of the x-ray examination apparatus, which proceeds through the length-adjustable support mounting 4, or the articulated arm 37, can be replaced by a corresponding displacement of the stand 1, 43. This can proceed such that, in this direction, known and therefore non-illustrated rails are laid on the floor or on the ceiling. The stand 1, 43 drives on these rails. It is advantageously also possible to merely suspend the stand 1, 43 from the ceiling.

Through the x-ray examination apparatus of the invention, with the x-ray tube, or the image layer carrier, respectively, a spherical movement path can be conducted since the movements of the apparatus parts are mechanically decoupled and the various movement paths are synchronously controlled via a control installation. Through the movement paths of the apparatus parts, also the support can be manufactured in a simple and cheap form.

Although various minor changes and modifications might be proposed by those skilled in the art, it will be understood that I wish to include within the claims of the patent warranted hereon all such changes and modifications as reasonably come within my contribution to the art.

I claim as my invention:

1. An x-ray examination apparatus, comprising:
a vertically extending stand;
a curved support having a radiation source mounted at one terminating end and an image layer carrier mounted at an opposite terminating end, the radiation source and image layer carrier being aligned to one another so that a central ray from the radiation source will strike the image layer carrier;
support mounting means for connecting the support to the stand for translational and rotational movement of the support relative to the stand; and
said support mounting means comprising, at its distal end opposite the stand, an end part having a first shaft projecting from one end thereof to which the support is directly mounted and about which the support rotates, a supporting shaft connecting to said stand, and a horizontal second shaft connecting the supporting shaft to the end part and which engages an opposite end of the end part, said second shaft being perpendicular to said first shaft and perpendicular to a direction of said central ray, the end part and the attached support pivoting about said second shaft so that the support pivots in a vertical plane.

2. An x-ray examination apparatus according to claim 1 wherein first drive means are provided for the rotation of the support about the first shaft and second drive means are provided for the pivotable movement of the end part about the second shaft, and wherein a first position sensor means is provided for detecting rotational position of the support and a second position sensor means is provided for detecting pivotable position of the end part.

3. An x-ray examination apparatus according to claim 2 wherein signals from the first and second position sensor means are transmitted to a control installation means which, given a specified isocenter in a body to be examined by the radiation source, and given a position change in one direction, determines controlled variables for the first and second drive means in such a fashion that through their actuation the isocenter is maintained.

4. An x-ray examination apparatus according to claim 1 wherein means are provided for translational movement of said stand relative to a floor.

5. An x-ray examination apparatus according to claim 1 wherein said support mounting means includes means for vertical movement of said support mounting means relative to the stand.

6. An x-ray examination apparatus, comprising:
a stand;
a support having a radiation source mounted at one end and an image layer carrier mounted at another, the radiation source and image layer carrier being aligned to one another so that a central ray from the radiation source will strike the image layer carrier;
support mounting means for connecting the support to the stand for translational and rotational movement of the support relative to the stand;
said support mounting means comprising at its distal end opposite the stand an end part having a first shaft connected thereto to which the support is mounted and about which the support rotates, a supporting shaft connected to said stand, a second shaft perpendicular to said first shaft connecting the end part to one end of the supporting shaft and about which the end part and the attached support pivots; and
the supporting shaft having means for adjusting a length thereof.

7. An x-ray examination apparatus, comprising:
a stand;
a support having a radiation source mounted at one end and an image layer carrier mounted at another, the radiation source and image layer carrier being aligned to one another so that a central ray from the radiation source will strike the image layer carrier;
support mounting means for connecting the support to the stand for translational and rotational movement of the support relative to the stand;
said support mounting means comprising at its distal end opposite the stand an end part having a first shaft connected thereto to which the support is mounted and about which the support rotates, a supporting shaft connecting to said stand, and a second shaft perpendicular to said first shaft connecting the supporting shaft to the end part and about which the end part and the attached support pivots; and
the supporting shaft being designed telescope-like and having a support shaft portion which receives a shaft extension portion, and wherein the second shaft is mounted at an end of the shaft extension portion.

8. An x-ray examination apparatus, comprising:
a stand;
a support having a radiation source mounted at one end and an image layer carrier mounted at another, the radiation source and image layer carrier being aligned to one another so that a central ray from the radiation source will strike the image layer carrier;
support mounting means for connecting the support to the stand for translational and rotational movement of the support relative to the stand;
said support mounting means comprising at its distal end opposite the stand an end part having a first shaft connected thereto to which the support is mounted and about which the support rotates, a supporting shaft connecting to said stand, and a second shaft perpendicular to said first shaft connecting the supporting shaft to the end part and about which the end part with the attached support pivots; and
means for pivotably mounting the supporting shaft to the stand so as to permit the supporting shaft and attached end part and support to swing in a vertical plane.

9. An x-ray examination apparatus, comprising:
a stand;
a support having a radiation source mounted at one end and an image layer carrier mounted at another, the radiation source and image layer carrier being aligned to one another so that a central ray from the radiation source will strike the image layer carrier;
support mounting means for connecting the support to the stand for translational and rotational movement of the support relative to the stand;
said support mounting means comprising at its distal end opposite the stand an end part having a first shaft connected thereto to which the support is mounted and about which the support rotates, a supporting shaft connecting to said stand, and a second shaft perpendicular to said first shaft connecting the supporting shaft to the end part and about which the end part with the attached support pivots; and
the supporting shaft comprising a two-part arm wherein the two parts are pivotably linked to one another.

10. An x-ray examination apparatus, comprising:
a stand;
a support having a radiation source mounted at one terminating end and an image layer carrier mounted at another opposite terminating end, the radiation source and image layer carrier being aligned to one another so that a central ray from the radiation source will strike the image layer carrier;
support mounting means for connecting the support to the stand for translational and rotational movement of the support relative to the stand;
said support mounting means comprising at its distal end opposite the stand an end part having a first shaft connected thereto to which the support is mounted and about which the support rotates, a supporting shaft connecting to said stand, and a second shaft perpendicular to said first shaft connecting the supporting shaft to the end part and about which the end part and the attached support pivots;
the supporting shaft being designed telescope-like with a supporting shaft portion and a shaft extension portion extensible from the shaft portion, and wherein the second shaft is mounted at an end of the shaft extension portion.

11. An x-ray examination apparatus, comprising:
a stand;
means for permitting translational movement of the stand relative to a floor;
a support having at one end a radiation source and at an opposite end imaging means, said radiation source being aimed and the support being shaped so that when radiation therefrom passes along a radiation path through a body isocenter being analyzed, rays are received by the imaging means; and
said support mounting means comprising at its distal end opposite the stand an end part having a first axle extending therefrom about which the support is rotatably mounted, a telescoping supporting shaft connecting to said stand, and a second axle connecting an extensible portion of the supporting shaft to the end part, said second axle being perpendicular to said first axle and being positioned to permit pivoting of the end part, and said first axle being perpendicular to the radiation path between the radiation source and imaging means.

* * * * *